US010441536B2

(12) United States Patent
Flynn et al.

(10) Patent No.: US 10,441,536 B2
(45) Date of Patent: Oct. 15, 2019

(54) MICRONIZED COLISTIMETHANE SODIUM PHARMACEUTICAL COMPOSITIONS

(71) Applicant: Forest Laboratories Holdings Limited, Hamilton (BM)

(72) Inventors: Richard Anthony Flynn, Kent (GB); Rahul Surana, Commack, NY (US); Anil Chhettry, Holtsville, NY (US); David Farrington, Garden City, NY (US); Ritesh Sanghvi, East Northport, NY (US)

(73) Assignee: ACTAVIS GROUP PTC EHF, Hafnarfjördr (IS)

( * ) Notice: Subject to any disclaimer, the term of this patent is extended or adjusted under 35 U.S.C. 154(b) by 0 days.

(21) Appl. No.: 14/772,748

(22) PCT Filed: Mar. 7, 2014

(86) PCT No.: PCT/US2014/021698
§ 371 (c)(1),
(2) Date: Sep. 3, 2015

(87) PCT Pub. No.: WO2014/164280
PCT Pub. Date: Oct. 9, 2014

(65) Prior Publication Data

US 2016/0022577 A1 Jan. 28, 2016

Related U.S. Application Data

(60) Provisional application No. 61/779,057, filed on Mar. 13, 2013.

(51) Int. Cl.
*A61K 9/00* (2006.01)
*A61K 9/14* (2006.01)
(Continued)

(52) U.S. Cl.
CPC ............ *A61K 9/0075* (2013.01); *A61J 1/035* (2013.01); *A61K 9/14* (2013.01); *A61K 9/145* (2013.01);
(Continued)

(58) Field of Classification Search
CPC ....... A61K 38/12; A61K 9/145; A61K 9/0075
See application file for complete search history.

(56) References Cited

U.S. PATENT DOCUMENTS

| | | | |
|---|---|---|---|
| 2004/0060265 A1 | 4/2004 | Boeckle et al. |
| 2007/0202053 A1 | 8/2007 | Bilzi et al. |
| 2011/0259328 A1 | 10/2011 | Villax et al. |

FOREIGN PATENT DOCUMENTS

| | | | |
|---|---|---|---|
| CN | 1321082 A | 11/2001 |
| RU | 2006133038 A | 3/2008 |

(Continued)

OTHER PUBLICATIONS

International Search Report for PCT/US2014/021698 dated Jun. 18, 2014.

(Continued)

*Primary Examiner* — Carlos A Azpuru
(74) *Attorney, Agent, or Firm* — Morgan, Lewis & Bockius LLP

(57) ABSTRACT

Described herein are micronized powder particles of colistimethate sodium wherein at least 50% by volume of the micronized particles have a diameter of less than 7 micrometers but not less than 3 micrometers and the powder has a total moisture content of from 5 to 10% by weight, for use in the treatment of a pulmonary infection by powder inhalation, wherein the colistimethate sodium is not separated into component form. The micronized powder particles of colistimethate sodium are useful in the treatment of infec-
(Continued)

Particle sizing of micronised colistin sulphomethate sodium tions caused by gram-negative bacteria, particularly in patients suffering from cystic fibrosis.

4 Claims, 5 Drawing Sheets

(51) Int. Cl.

| | |
|---|---|
| ***A61K 9/48*** | (2006.01) |
| ***A61K 38/12*** | (2006.01) |
| ***A61J 1/03*** | (2006.01) |
| ***A61K 45/06*** | (2006.01) |
| ***B65D 75/36*** | (2006.01) |

(52) U.S. Cl.

CPC .......... *A61K 9/4825* (2013.01); *A61K 9/4858* (2013.01); *A61K 38/12* (2013.01); *A61K 45/06* (2013.01); *B65D 75/367* (2013.01); *Y02A 50/473* (2018.01)

(56) References Cited

FOREIGN PATENT DOCUMENTS

| | | | | |
|---|---|---|---|---|
| WO | 00/16745 A2 | | 3/2000 | |
| WO | 2000/016745 | * | 3/2000 | |
| WO | 0016745 A2 | * | 3/2000 | .......... A61K 9/0075 |
| WO | 2007045689 A2 | | 4/2007 | |
| WO | 2012/061902 A1 | | 5/2012 | |

OTHER PUBLICATIONS

European Search Report for European Patent Application No. 14 778 370.8 dated Sep. 19, 2016.

Lolodi: "Microencapsulation of colistin 1-12 sodium methanesulfonate in gum arabic and maltodextrin by spray trying", Trends in Applied Sciences Research, vol. 6, No. 8, 2011, pp. 877-889.

Written Opinion for Singapore Application No. 11201507466X dated Aug. 17, 2016.

De Boer, A. H. et al., Design and in vitro performance testing of multiple air classifier technology in the twincer®. European Journal of Pharmaceutical Sciences, 8 Mar. 2006, vol. 28, No. 3, pp. 171-178.

Search Report for Singapore Application No. 11201507466X dated May 19, 2016.

Westerman et al: "Dry powder inhalation 1-12 of colistin in cystic fibrosis patients: a single dose pilot study". Journal of Cystic Fibrosis. Elsevier, NL, vol. 6, No. 4, 2007, pp. 284-292.

Written Opinion for PCT/US2014/021698 dated Jun. 18, 2014.

Chinese Office Action, dated May 4, 2017, issued in corresponding Chinese Application No. 201480025155.9.

Search Report, dated Apr. 25, 2017, issued in corresponding Chinese Application No. 201480025155.9.

Russian Office Action dated Oct. 23, 2017 issued in co-pending Russian application 2015143135/15.

Notice of Substantive Examination Report issued in co-pending Saudi Arabian patent application No. 515361081, dated Dec. 18, 2017.

European Pharmacopoeia, 7th Edition, pp. 1762-1763 (2013).

Australian Examination Report No. 1 for AU 2014249529, dated Nov. 24, 2017; 3 pages.

English Translation of Chinese Office Action for Appl. No. 201480025155.9, dated Dec. 26, 2017; 10 pages.

* cited by examiner

Particle sizing of micronised colistin sulphomethate sodium

COLISTIN SULPHOMETHATE Sodium

R1=  OR  OR

R2=  OR  OR

COLISTIN BASE

R1=  OR

R2=  OR mentioned in text but not in drawing

MICRONIZED COLISTIMETHANE SODIUM PHARMACEUTICAL COMPOSITIONS

CROSS-REFERENCE TO RELATED APPLICATIONS

This application claims priority from U.S. Provisional Application 61/779,057, filed Mar. 13, 2013, the contents of which are incorporated herein by reference in their entirety.

TECHNICAL FIELD

The present disclosure describes improvements in or relating to pharmaceutical compositions comprising micronized colistin sulphomethate sodium.

BACKGROUND OF THE INVENTION

Colistin is an anti-bacterial cationic cyclic polypeptide belonging to the polymixin group. It is produced as a secondary metabolite of *Bacillus polymyxa* var. *colistinus*. Treatment of colistin base with formaldehyde and sodium bisulphite produces colistin sulphomethate sodium. The product is a crystalline powder which is soluble in water.

Colistin sulphomethate sodium, more commonly referred to as colistimethate sodium is a combination of the negatively charged molecular ion colistin sulphomethate with positive sodium ions. It should be carefully distinguished from colistin sulphate. Both are described in the European Pharmacopoeia.

Colistin is of particular benefit in the treatment of serious infections caused by bacterial pathogens such as *Pseudomonas aeruginosa, Escherichia coli* and *Klebsiella* spp. An important property of colistin is that bacteria sensitive to the drug do not readily acquire resistance. Colistin as a pharmaceutical may be prepared in numerous different preparations, e.g., topical, bladder irrigation, oral such as tablets, or as intravenous or intra-muscular injections.

Colistimethate sodium is a white to slightly yellow hygroscopic powder. It is commercially supplied at a particle size of 100-200 μm mass median diameter. The powder is highly soluble in water, slightly soluble in ethanol (96%) and is used for parenteral administration by dissolving in water. As a powder, colistin sulphomethate sodium must be stored in air-tight containers, preferably protected from light. Colistin sulphomethate sodium is used to treat infections in patients suffering from cystic fibrosis, a genetic disease which affects many body systems, and which develops at a young age. The disease is marked by a malfunction of the glands in the lining of the bronchial tubes. Instead of producing their normal thin mucus, the bronchial glands produce thick, sticky mucus that stagnates in the bronchial tubes. Microbes are able to multiply readily, causing serious respiratory infections, ultimately leading to respiratory failure. It is known that colistimethate sodium is effective in treatment of infections caused by these microbes e.g., *Pseudomonas aeruginosa*. The usual form of administration is as a solution for inhalation after nebulisation. The nebulised solution is prepared by taking a vial in which there is a known dosage of colistimethate sodium powder, injecting water into the vial and then inhaling the solution into the lungs through a nebuliser. Colistimethate sodium is poorly absorbed into the bloodstream. Therefore, this method of administration is preferred since bacteria can be attacked in the mucus which lines the lungs during illness.

Although colistin sulphomethate sodium is a valuable pharmaceutical in the treatment of infections occurring during cystic fibrosis and other bacterial infections, there are a number of disadvantages in drug delivery that have impeded acceptance as a treatment regime for cystic fibrosis, particularly for infants. It has been determined that many of the problems arise from the preferred delivery method described above, i.e., as a nebulised liquid. The present invention described herein addresses and solves this long-felt need in the art.

SUMMARY OF THE INVENTION

The present disclosure describes improvements in or relating to pharmaceutical compositions comprising micronized colistin sulphomethate sodium.

In one aspect of the present invention, at least about 50% by volume of the micronized particles have a diameter of less than about 7 micrometres but not less than about 3 micrometres and the powder has a total moisture content from about 0.1 to about 10% by weight, for use in the treatment of a pulmonary infection by powder inhalation, wherein the colistimethate sodium is not separated into component form.

In one embodiment, about 10% by volume of the particles have a particle size of less than about 3 micrometres but not less than about 1.5 micrometres.

It has been found that the use of larger particles for inhalation in comparison to the normal size of from 2 micrometres to 5 micrometres has advantageous effects related to physical stability of the powder when filled into a product capsule, and in preventing powder compaction within the capsule. Larger particles act as carriers into the lungs for smaller particles.

A further surprising outcome of this approach to particle size is that the amount of colistimethate sodium is delivered very deep into the lungs with subsequent absorption into the blood stream with dramatically reduced toxicity while maintaining sufficient levels for the desired clinical outcome when compared to particles of a smaller average size.

According to one aspect of the present invention, a pharmaceutical dosage form suitable for use with a dry powder inhaler is provided. The dosage form includes (a) micronized powder particles of colistimethate sodium wherein at least about 50% by volume of the micronized particles have a diameter of less than about 7 micrometres but not less than about 3 micrometres and the powder has a total moisture content from about 0.1 to about 10% by weight, for use in the treatment of a pulmonary infection by powder inhalation, wherein the colistimethate sodium is not separated into component form; (b) a container for the micronized powder particles of colistimethate sodium. According to an embodiment of the present invention, the container is a hard gelatin capsule.

In another aspect, a pharmaceutical capsule having micronized powder particles of colistimethate sodium is provided, wherein at least about 50% by volume of the micronized particles have a diameter of less than about 7 micrometres but not less than about 3 micrometres and the powder has a total moisture content of from about 0.1 to about 10% by weight, for use in the treatment of a pulmonary infection by powder inhalation, wherein the colistimethate sodium is not separated into component form. In one embodiment of the present invention, the pharmaceutical capsule is translucent. In another embodiment, the pharmaceutical capsule has a micronized bronchodilatory drug.

According to another aspect, the pharmaceutical capsule has between 1,500,000 and 2,000,000 IU of colistimethate sodium. In one embodiment, a blister pack comprising aluminium foil together with a plurality of pharmaceutical capsules is provided.

In another aspect of the present invention, a method of treating gram-negative infections of the respiratory tract is provided. The method includes administering micronized powder particles of colistimethate sodium to the respiratory tract of a patient, wherein at least about 50% by volume of the micronized particles have a diameter of less than about 7 micrometres but not less than about 3 micrometres and the powder has a total moisture content of from about 0.1 to about 10% by weight, wherein the colistimethate sodium is not separated into component form.

According to one embodiment, a method of treating a patient suffering from gram-negative infections of the respiratory tract is provided, wherein the patient is a paediatric patient. In another embodiment, the gram-negative infections are caused by bacterial pathogens selected from a group having *Pseudomonas aeruginosa, Escherichia coli* and *Klebsiella* spp.

In another aspect of the present invention, micronized colistimethate sodium in a pharmaceutical dosage form with a dry powder inhaler is provided. The micronized colistimethate sodium powder has moisture content from about 0.1 wt % to about 10 wt %. The micronized powder is provided optionally together with a carrier, and a container. In one embodiment, the container is preferably a capsule. According to another embodiment, the moisture content of micronized colistimethate sodium is from about 5 wt % to about 10 wt %.

The present invention also describes pharmaceutical composition having colistimethate sodium powder for use in capsules is provided, where the moisture content of the powder is controlled by using the capsule as a moisture buffer. According to one embodiment, the moisture content of the capsule ranges from about 0.1 wt % to about 16 wt %.

In another embodiment, a gelatin capsule with capsule shell water content from about 6 wt % to about 16 wt % is provided. The gelatin capsule may be a PEG based gelatin capsule with capsule shell water content from about 5 wt % to about 15 wt %. In another embodiment, the capsule may be a hydroxypropyl methyl cellulose (HPMC) capsule with capsule shell water content from about 0.1 wt % to about 10 wt %.

As described herein in the following Detailed Description and drawings, the present disclosure results in improvements in storage stability, decreases moisture transfer and increases stability and operability of colistimethate sodium.

DEFINITIONS

Figure 1:
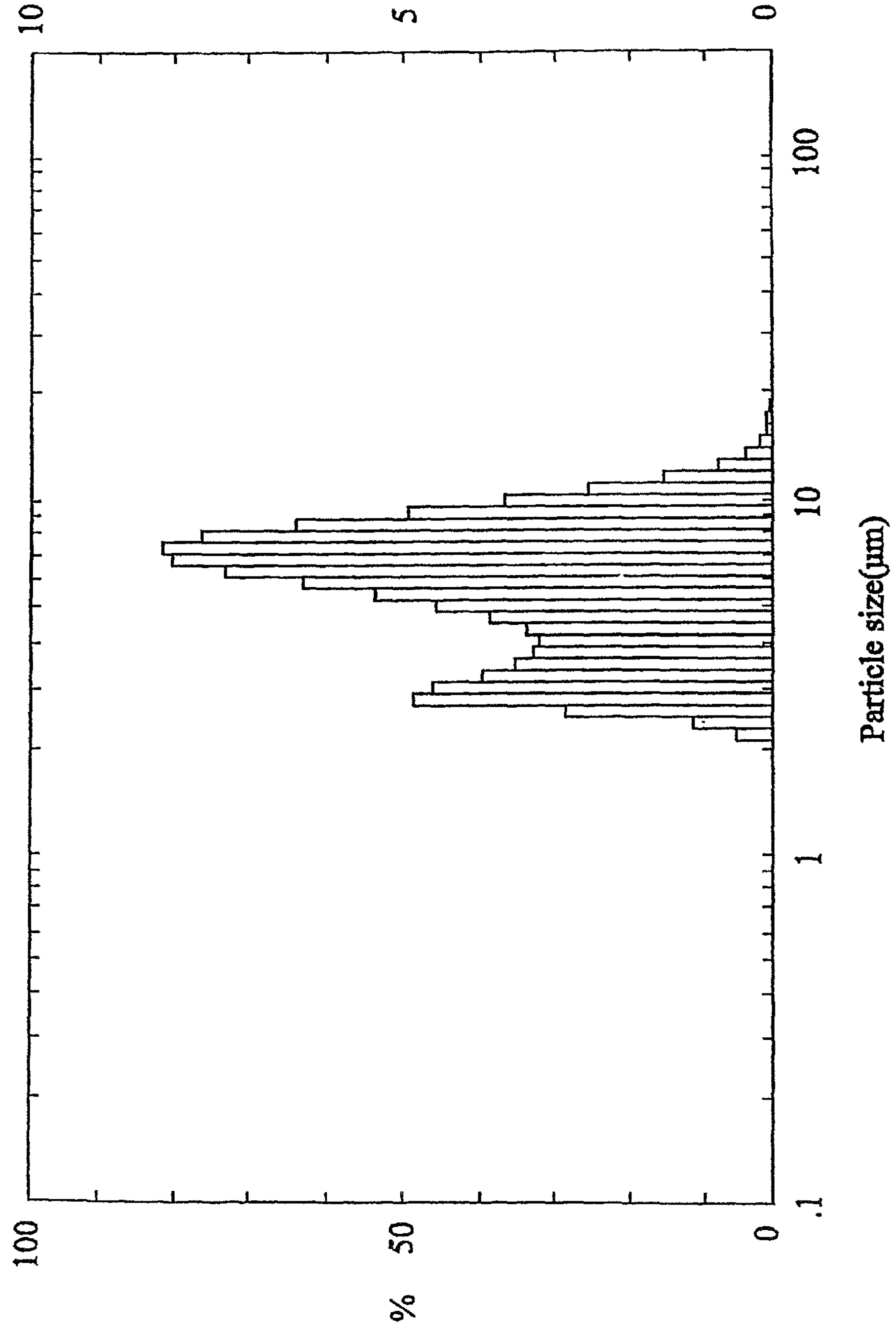
FIG. 1 shows a particle size analysis of micronized colistin sulphomethate sodium.

The term "respirable dry powder" refers to a composition that has finely dispersed particles that are relatively free flowing and capable of (i) being readily dispersed in an inhalation device and (ii) inhaled by a subject so that at least a portion of the particles reach the lungs to permit penetration to the alveoli. The dry powder may be crystalline, amorphous or a mixture of both (partially crystalline). Such powder is considered to be "respirable" or "inhalable", more particularly, suitable for pulmonary delivery. Although a preferred embodiment is directed to respirable dry powder formulation of colistimethate sodium, the present invention may be practiced for formulations intended for other routes of administration, such as oral administration.

The term "emitted dose" or "ED" refers to an indication of the delivery of the formulation from a suitable inhaler device after a firing or dispersion event. More specifically, for colistimethate sodium formulation, the ED is a measure of the percentage of powder which is drawn out of a unit dose package and which exits the mouthpiece of an inhaler device.

The term "aerosolized" refers to a gaseous suspension of fine dry powder or liquid particles. An aerosolized medicament may be generated by a dry powder inhaler, a metered dose inhaler, or a nebulizer.

The term "dispersible" powder is one having an ED value of at least about 30%, preferably at least about 40%, more preferably at least about 50%, more preferably at least about 60%, more preferably at least about 70%, more preferably at least about 80%, more preferably at least about 90%.

The term "dispersing agent" refers to a component of the respirable dry powder formulation that is effective, when present, from 0.01 to 99 percent by weight of the composition, preferably from 0.01 to 70 percent by weight, to increase the dispersibility of the respirable dry powder formulation of colistimethate sodium as determined by emitted dose determination by at least 10% when compared to the dispersibility of the respirable dry powder formulation without the dispersing agent. Any suitable dispersing agents known in the art may be used.

Maximum critical moisture content of colistimethate sodium is the point at which colistimethate sodium powder begins to lose its chemical and physical stability (including aerosol properties) and storage stability. Minimum critical moisture content of colistimethate sodium is the point at which colistimethate sodium dry powder begins to lose its mechanical integrity and/or dispersibility, such that performance of the dry powder is adversely affected. The critical moisture (maximum or minimum) content varies from one colistimethate sodium dry powder formulation to the next and can be readily determined by one skilled in the art, using routine experimentation. Minimum RH and maximum RH refers to the level of relative humidity corresponding to critical moisture point.

Maximum critical moisture content of the capsule is the point at which capsule having colistimethate sodium begins to lose its chemical and physical stability. Minimum critical moisture content of the capsule is the point at which capsule having colistimethate sodium begins to lose its mechanical integrity. The critical moisture (maximum or minimum) content varies with different colistimethate sodium dry powder formulations and with different type of capsules and can be readily determined by one skilled in the art, using routine experimentation. RH of capsule refers to the level of relative humidity corresponding to critical moisture point.

The term "desiccant", also known as a drying agent, is a material that absorbs or adsorbs water and is used to remove environmental moisture. Desiccants necessarily have a high affinity for water. Examples include calcium oxide, molecular sieves and silica gels. Desiccants primarily act to keep the dry powders sufficiently "dry" (i.e., below the critical moisture point).

DETAILED DESCRIPTION OF THE INVENTION

Whilst jet nebulisation therapy has been shown to be successful, the nebulisation technique has several drawbacks. Jet nebulisers utilise compressed gases (usually air) to convert a drug solution into a spray. The compressed air passes through a narrow venturi orifice and a negative pressure is created. Liquid drawn from a fluid reservoir through a feed tube fragments into droplets, and is accelerated to a velocity sufficient for more than 99% of the droplet mass to impact on baffles or on the nebuliser where droplets coalesce and drain back into the fluid reservoir. Only 1% of the aerosol mass leaves the nebuliser directly. The outgoing air becomes saturated with water derived from liquid retained in the nebuliser. This has two important consequences: Firstly, the nebuliser is cooled and reaches an equilibrium temperature approximately 10° C. below ambient, so that the patient inhales a relatively cold spray. Secondly, the evaporation of water causes the concentration of solutes to increase with time.

There are many different designs of nebuliser available that use different flow rates of compressed gas. The output from these nebulisers will all be different and accordingly it is difficult for a patient to ensure that a constant dose is administered. The nebulisers themselves are bulky due to the compressors which are required. Although described as being transportable, the nebuliser/compressor system is not truly portable. When patients are undergoing treatment, they need to remain connected to the mouthpiece of the nebuliser for approximately 20 minutes in order to complete the therapy and to ensure that the correct dose is administered. Further, an electrical supply is needed to run the nebuliser.

Surprisingly and unexpectedly, moisture content of micronized colistimethate sodium from about 0.1 wt % to about 10 wt % improves the flow of the powder into the lungs without adversely affecting the stability of the final product. Further, the flow properties of the micronized formulation may be also be improved by changing relative humidity and/or temperature conditions during manufacturing and packaging of the formulation. Flow properties may also be improved by exposing colistimethate sodium (dry) powder to ambient conditions before filling. Surprisingly and unexpectedly, the rate of breakage and/or malfunctioning of the capsule may be decreased by carefully controlling the characteristics of the capsule. Above described methods for improving flow properties of colistimethate sodium and preventing the rate of breakage of the capsules are considered as separate embodiments of the present invention.

In order for the nebuliser to function properly, respirable colistimethate sodium powder must be formulated and dispensed carefully. Characteristics such as, but not limited to, moisture content of colistimethate sodium powder, the hygroscopic nature of the powder, environmental conditions during manufacturing and packaging should be carefully controlled. Changes in moisture content of colistimethate sodium could affect the flowability of the respirable powder. Changes in moisture content of a capsule having colistimethate sodium powder could change the brittleness of the capsule, leading to breakage and/or malfunctioning of the capsule.

Figure 2:
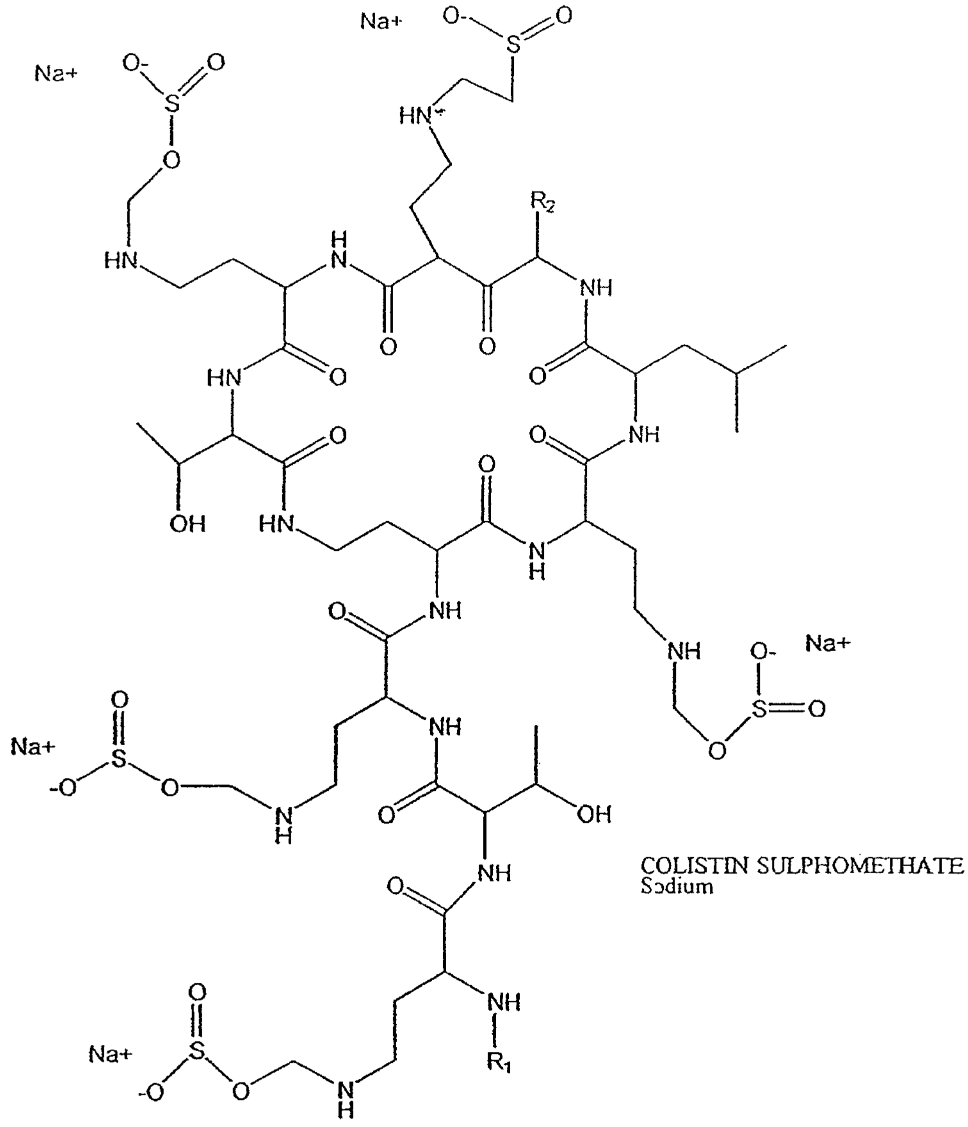
FIG. 2 shows the structure of colistin sulphomethate with accompanying sodium ions.
Figure 2:
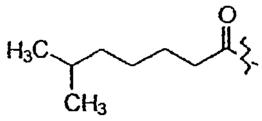
Figure 2:
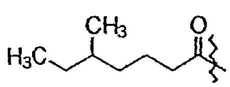
Figure 2:
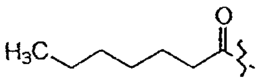
Figure 2:
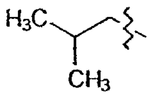
Figure 2:
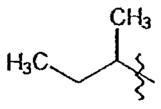
Figure 2:
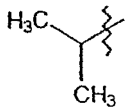
Figure 3:
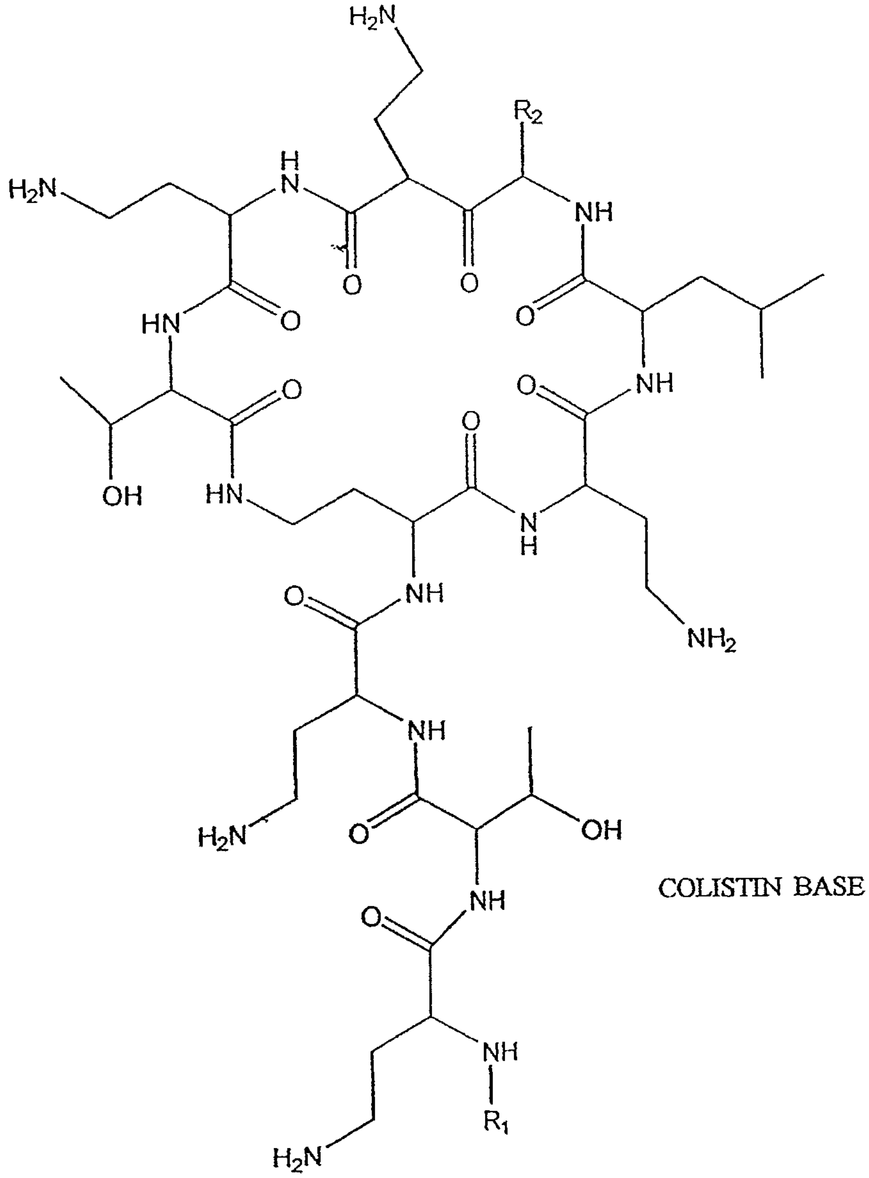
FIG. 3 shows a neutralised colistin base, as described in U.S. Pat. No. 5,767,068.
Figure 3:
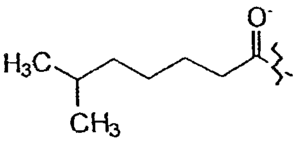
Figure 3:
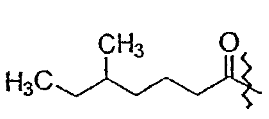
Figure 3:
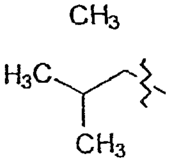
Figure 3:
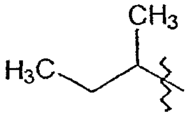
Figure 3:
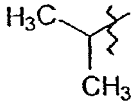

FIG. 1 shows a particle size analysis of micronized colistin sulphomethate sodium. Colistimethate sodium is a negatively charged molecular ion with positively charged sodium counter ions. FIG. 2 shows the structure of colistimethate sodium. There are five sulphomethate groups ($CH_2$—$OS0_2^-$). In contrast, U.S. Pat. No. 5,767,068 discloses a neutral base as shown in FIG. 3. U.S. Pat. No. 5,767,068 refers to variable groups $R_x$ and $R_2$; $R_x$ is identified as 6-methyloctanoyl or 6-methylheptanoyl, and $R_2$ as sec-butyl, isobutyl or isopropyl. It has been found that colistimethate sodium is a mixture of at least ten components. Tests carried out on mixtures of antibacterial preservatives show that the mixture of components found in colistimethate sodium show synergy of activity against gram negative microbial organisms.

Micronized colistimethate sodium according to the present invention is a powder wherein about 90% by volume of the powder has particles which have a diameter of less than about 10 micrometres. Preferably, about 50% by volume of the particles have a diameter of less than about 7 micrometres but not less than about 3 micrometres and about 10% by volume of the particles have a particle size less than about 3 micrometres but not less than about 1.5 micrometres. As absorption into the blood stream is not wanted, the negatively charged ion is preferred to the base colistin.

Medicaments for administration by inhalation should be of a controlled particle size to achieve maximum penetration into the lungs. Suitable particle size range from about 0.01-10 micrometres, preferably about 1-8 micrometres. Particle size may be measured by a number of methods, such as laser diffraction or microscopic analysis. Micronized colistimethate sodium may be prepared by fluid energy milling, ball milling, spray drying or precipitation.

Surprisingly, micronized powder of colistimethate sodium does not stick together and the micronized particles can be delivered to the alveoli of the lungs. Absorption of water by micronized powder is comparatively low, e.g., approximately about 0.1%40% by weight under normal atmospheric conditions. Negatively charged colistin sulphomethate ion, preferably in its sodium form can be delivered to the lungs when the micronized colistimethate sodium powder is present with a moisture content of about 5 wt %, about 5.5 wt %, about 6 wt %, about 6.5 wt %, about 6.75 wt %, about 7 wt %, about 7.25 wt %, about 7.5 wt %, about 7.75 wt %, or about 8 wt %. The micronized colistimethate sodium powder may be present with moisture content in a range of about 0.1 wt % to about 10 wt %. The actual moisture content may be present in any increments within the range.

In another aspect, negatively charged colistin sulphomethate ion, preferably in its sodium form can be delivered to the lungs when the micronized colistimethate sodium powder is present with a minimum critical moisture content of about 0.1 wt % and a maximum critical moisture content of about 10 wt %. In some embodiments, the minimum critical moisture content is about 4 wt % and the maximum critical moisture content of about 10 wt %. In other embodiments, the minimum critical moisture content is about 5 wt % and the maximum critical moisture content is about 10 wt %. The micronized colistimethate sodium powder may be present with a minimum critical moisture content of about 6 wt % and a maximum critical moisture content of about 10 wt %. In other embodiments, the minimum critical moisture content is about 6.5 wt % and the maximum critical moisture content is about 10 wt %. In some embodiments, the micronized colistimethate sodium powder is present with a minimum critical moisture content of about 5 wt % and a maximum critical moisture content of about 9 wt %. In other embodiments, the minimum critical moisture content is about 5 wt % and the maximum critical moisture content is about 8 wt %. In another embodiment, the micronized colistimethate sodium powder is present with minimum critical moisture content of about 5.5 wt % and a maximum critical moisture content of about 8 wt %.

The minimum relative humidity (RH) may be above 2% RH, ±5% RH. In certain embodiments, the minimum relative humidity is above 2% RH, above 4% RH, above 6%, above 10% RH, above 12% RH, above 15% RH, above 25% RH, above 30% RH, above 40% RH, above 45% RH, above 60% RH, ±5% RH at 23° C., ±2° C. In other embodiments, the minimum relative humidity is at about 26° C., 27° C., 28° C. or 30° C., ±2° C.

In some embodiments, the maximum relative humidity is less than 75% RH, ±5% RH. In For example, the maximum relative humidity may be less than 50% RH, less than 40% RH, less than 30% RH, less than 20% RH, less than 10% RH, less than 5% RH, ±5% RH at 23° C.±2° C. In some embodiments, the maximum relative humidity is at about 26° C., 27° C., 28° C. or 30° C., ±2° C. The relative humidity may be present in a range of about 2% RH to about 75% RH. The actual relative humidity may be present in any increments within the range.

The relative humidity may be selected such that the equilibrium of moisture content of colistimethate sodium powder does not exceed its maximum critical moisture content and is not less than the minimum critical moisture content, thereby ensuring flowability and storage stability of colistimethate sodium powder at room temperature.

The present invention also provides a method for preparing a composition of the invention which comprises mixing together micronized colistimethate sodium and optionally a carrier. The colistimethate sodium and the carrier may be blended in a drum, hoop or Y-cone blender as known in the art.

Colistimethate sodium may be administered in conjunction with a carrier. The carrier may be any non-toxic material which is chemically inert to the colistimethate sodium and will be acceptable for inhalation or for administration. Examples of carriers without limiting include inorganic salts, e.g., sodium chloride or calcium carbonate; organic salts, e.g., sodium tartrate or calcium lactate; organic compounds, e.g., urea; monosaccharides, e.g., lactose, arabinose or dextrose; disaccharides, e.g., maltose or sucrose; polysaccharides, e.g., starches and dextrans. A particularly preferred carrier is lactose, e.g., crystalline lactose.

The carrier may have a particle size specification same as colistimethate sodium powder. If a carrier is used, it is preferred that the carrier has a larger particle size than that of the colistimethate sodium to facilitate delivery from the inhalation device and yet not be deposited in the finer airways of the lungs. Inclusion of a carrier may ease dosage of pharmaceutical and carrier into capsules. Preferably, at least about 50%, and more preferably, at least about 70% by volume of the carrier particles have an effective particle size in the range of about 30 micrometres to about 150 micrometres, preferably about 30 micrometres to about 80 micrometres. The admixture of pharmaceutical and carrier may contain up to about 75% by weight, more preferably up to about 50% by weight of carrier. Generally the ratio of colistimethate sodium is about 5:1 to 1:2, preferably about 4:1 to 1:1 by weight.

In addition to the micronized colistimethate sodium, excipients, and optionally, the carrier, the pharmaceutical composition may also have other ingredients, such as colouring matter or flavouring agents such as saccharine, which may be present in inhalant compositions. Antistatic agents may also be added, as described in GB 2269992 (Rhone-Poulenc Rorer Ltd). The powder formulation may have other pharmaceutical ingredients such as bronchodilators e.g., salbutamol. Such other pharmaceutical ingredients preferably have an effective particle size similar to that of the colistin. The bronchodilatory drug will be delivered in very small (milligram (mg)) quantities. For example a capsule may have from about 50 milligrams to about 150 milligrams, e.g., 125 milligrams of colistimethate sodium and from about 1 milligram to about 250 milligrams, e.g., 200 micrograms of salbutamol.

The micronized powder may be delivered to the lungs through a specialised powder inhalation device. Preferably, the powdered pharmaceutical drug is within a hard capsule or a blister package. The capsule or blister is ruptured or broached with an inhaler device, thereby enabling the powder to be inhaled through the mouthpiece as air is sucked in.

Moisture content of the capsule shell may have a direct impact on the piercing and/or functioning of the capsule when the capsule is actuated using the inhaler device. Surprisingly and unexpectedly, the rate of breakage and/or malfunctioning of the capsule may be decreased by carefully controlling the characteristics of the capsule, such as, but not limited to, moisture content of the capsule, relative humidity, and/or the conditions at which the capsules and/or blisters are filled. Similarly, flowability of colistimethate sodium powder may be enhanced by carefully controlling the physical and chemical characteristics of colistimethate sodium powder, such as, but not limited to, moisture content and relative humidity.

According to an embodiment of the invention, a dosage unit having a capsule comprising colistin sulphomethate sodium is provided. The capsule may be formed of gelatin or a plastics material. Preferred capsule for use in the present invention are those formed from a PEG-based gelatin capsules or from a water-soluble cellulose derivative. Examples of water-soluble cellulose derivatives include microcrystalline cellulose and cellulose esters substituted with alkyl groups, especially $C_1$ to $C_4$ lower alkyl groups, and/or hydroxyalkyl groups, especially $C_1$ to $C_4$ hydroxy lower alkyl groups. Specific examples include, but are not limited to, hydroxypropyl methyl cellulose (HPMC), hydroxyethyl cellulose, hydroxypropyl cellulose, and hydroxyethyl methyl cellulose. The preferred cellulose derivative is hydroxypropyl methyl cellulose (HPMC).

The capsule material may further have a polymerizing additive. There is no specific limit on the capsule material, as long as it has the requisite chemical and physical characteristics described herein. Various size capsules are suitable for the present invention, including No. 00, No. 1, No. 2, and No. 3 capsules. Capsules formed using water-soluble cellulose derivatives are available in different colors, opacities, and grades, all of which are contemplated for use according to the present invention. The powder formulations for use with the present invention are known in the art. Such formulations may comprise active agents, dispersing agents, and excipients as known in the art.

Capsule of the present invention may include a water-soluble cellulose compound and a gelling agent. Cellulose ethers substituted with at least one group of alkyl groups and hydroxyalkyl groups can be mentioned as usable water-soluble cellulose compounds for the invention. The “alkyl group” and “hydroxyalkyl groups” refers to linear or branched lower alkyl groups having 1 to 6 carbon atoms, and preferably 1 to 4 carbon atoms, and a methyl group, an ethyl group, a butyl group, and a propyl group can be specifically mentioned. Specific examples of water-soluble cellulose compounds include lower alkylcelluloses, such as methylcellulose and the like, lower hydroxyalkyl celluloses, such as hydroxyethylcellulose, hydroxypropylcellulose, and the like, and lower hydroxyalkyl alkylcelluloses, such as hydroxyethyl methylcellulose, hydroxyethyl ethylcellulose, hydroxypropyl methylcellulose, and the like. Hydroxypropyl methylcellulose is particularly suitable due to the film formability and mechanical strength under low moisture conditions.

Carrageenan, tamarind seed polysaccharide, pectin, xanthan gum, locust bean gum, curdlan, gelatin, fur selenium, agar, gellan gum, etc. are usable gelling agents, alone or in combination. Among the above-mentioned gelling agents, carrageenan has high gel strength and exhibits an excellent gelling ability when used in a small amount and in combination with specific ions.

A gelling aid can also be used depending on the kind of gelling agent used. The following gelling aids may be used in combination with a carrageenan as the gelling agent. For κ-carrageenans, compounds that yield one or more kinds of potassium ion, ammonium ion, and calcium ion in water, such as potassium chloride, ammonium chloride, ammonium acetate, and calcium chloride may be used. For τ-carrageenans, compounds that yield a calcium ion in water, such as calcium chloride may be used. As gelling aids used in combination with a gellan gum as the gelling agent, compounds that yield one or more kinds of sodium ion, potassium ion, calcium ionized, and magnesium ion in water, such as sodium chloride, potassium chloride, calcium chloride, and magnesium sulfate may be used. In addition, citric acid or sodium citrate may also be used as an organic acid or a water-soluble salt thereof. Preferably, hydroxypropyl methylcellulose may be used as a water-soluble cellulose compound, carrageenan as a gelling agent, and a gelling aid.

In addition to the above-mentioned components, plasticizers, colorants, for example, dyes, pigments, opacifying agents or flavoring agents may also be added, as required. Any plasticizers may be used without limitation insofar as they can be used for medical drugs or food products. For example, dioctyl adipate, polyester adipate, epoxidated soybean oil, epoxy hexahydro phthalic acid diester, kaolin, triethyl citrate, glycerol, glycerol fatty acid ester, sesame oil, a polydimethylsiloxane-silicon dioxide mixture, D-sorbitol, medium chain fatty acid triglyceride, sugar alcohol solution originated corn starch, triacetin, concentrated glycerin, castor oil, phytosterol, diethyl phthalate, dioctyl phthalate, dibutyl phthalate, butyl phthalyl butyl glycolate, propylene glycol, polyoxyethylene (105) polyoxy-propylene (5) glycol, polysorbate 80, macrogol 1500, macrogol 400, macrogol 4000, macrogol 600, macrogol 6000, isopropyl myristate, cotton seed oil-soybean oil mixture, glyceryl monostearate, isopropyl linolate, may be used as plasticizers. Any colorants may be used without limitation insofar as they can be used for medical drugs or food products. For example, powdered catechutannic acid, turmeric extract, methylrosanilinium chloride, yellow iron oxide, yellow iron sesquioxide, orange essence, brown iron oxide, carbon black, caramel, carmine, carotene liquid, β-carotene, light sensitive element No. 201, licorice extract, gold leaf, sasa albomarginala extract, black iron oxide, light anhydrous silicic acid, kekketsu, zinc oxide, titanium oxide, iron sesquioxide, disazo yellow, food blue No. 1 and its aluminum lake, food blue No. 2 and its aluminum lake, food Yellow No. 4 and its aluminum lake, food Yellow No. 5 and its aluminum lake, food Green No. 3 and its aluminum lake, food red No. 2 and the aluminum lake, food red No. 3, food red No. 102 and its aluminum lake, food red No. 104 and its aluminum lake, food red No. 105 and its aluminum lake, food Red No 106 and its aluminum lake, sodium hydroxide, talc, copper chlorofin sodium, copper chlorophyll, rye green leaf juice powder, rye green leaf extract, phenol red, sodium fluorescein, d-borneol, malachite green, octyl dodecyl myristate, methylene blue, medicinal carbon, riboflavin butyrate, riboflavin, powdered green tea, manganese ammonium phosphate, riboflavin sodium phosphate, rose oil, turmeric color, chlorophyll, carminic acid color, food red No. 40 and its aluminum lake, water-soluble annatto, sodium iron-chlorophyllin, dunaliella carotene, paprika colour, ginseng carotene, potassium norbixin, sodium norbixin, palm oil carotene, beat red, grape pericarp color, black currant color, monascus color, safflower red color, safflower yellow color, marigold color, sodium riboflavine phosphate, madder color, alkanet color, aluminum, potato carotene, shrimp color, krill color, orange color, cacao color, cacao carbondust color, oyster color, crab color, carob color, fish scale foil, silver, kusagi color, gardenia blue color, gardenia red color, gardenia yellow color and kooroo color, chlorophine, kaoliang color, bone char color, bamboo grass color, shea nut color, lithosperm root color, redsanders color, vegetable carbon black, sappan color, spirulina color, onion color, tamarind color, corn color, tomato color, peanut color, phaffia color, pecan nut color, monascus yellow, powdered annatto, hematococcus algae color, purple sweet potato color, purple corn color, purple yarn color, vegetable oil soot color, lac color, rutin, enju extract, backwheat extract, logwood color, red cabegge color, red rice color, red color, azuki color, hydrangeae leaves extract, sepia color, uguisukagura color, elderberry color, olive tea, cowberry color, gooseberry color, cranberry color, salmon berry color, strawberry color, dark sweet cherry color, cherry color, thimbleberry color, deberry color, pineapple juice, huckleberry juice, grape juice color, black currant color, blackberry color, plum color, blueberry color, berry juice, boysenberry color, whortleberry color, mulberry color, morello cherry color, raspberry color, red currant color, lemon juice, loganberry color, powdered chlorella, cocoa, saffron color, beefsteak plant color, chicory color, layer color, hibiscus color, malt extract, powdered paprika, beet red juice, ginseng juice, may be used as colorants. Any opacifying agents or flavoring agents may be used without limitation insofar as they can be used for medical drugs or food products. For example, as opacifying agents, titanium oxide, iron sesquioxide, yellow iron sesquioxide, black iron oxide, food blue No. 1 aluminum lake, food blue No. 2 aluminum lake, food yellow No. 4 aluminum lake, food yellow No. 5 aluminum lake, food green No. 3 aluminum lake, food red No. 2 aluminum lake, food red No. 3 aluminum Lake, food red No. 102 aluminum lake, food red No. 104 aluminum lake, food red No. 105 aluminum lake, food red No. 106 aluminum lake, and food red No. 40 aluminum lake may be used as opacifying agents.

The capsule of the present invention has low equilibrium moisture content. The equilibrium moisture of the capsule can be evaluated from the moisture content of the capsule film when a capsule is placed under a specific relative humidity condition.

The water-soluble cellulose compound is about 5 to 30% by weight, preferably about 10 to 28% by weight, and more preferably about 16 to 24% by weight. The gelling agent is about 0.01 to 0.5% by weight, preferably about 0.02 to 0.45% by weight, and more preferably about 0.03 to 0.4% by weight. The gelling aid, if added, is about 0.01 to 0.5% by weight, preferably about 0.02 to 0.45% by weight, and more preferably about 0.03 to 0.4% by weight.

As described herein, the moisture content of the capsule shell may have a direct impact on the piercing and functioning of the capsule. In one embodiment, breakage of capsules may be controlled by modifying the physical and chemical characteristics of the capsule, such as, but not limited to, moisture content of the capsule, relative humidity, and/or the conditions at which the capsules and/or blisters are filled. In another embodiment, breakage of capsules may be controlled by controlling the physical and chemical characteristics of colistimethate sodium powder, such as, but not limited to, moisture content and relative humidity.

Gelatin capsules adsorb moisture readily and equilibrate to the environmental humidity conditions. Gelatin capsules having micronized colistimethate sodium powder as described herein may have a moisture content of about 6 wt %. In other embodiments, the gelatin capsule may have a moisture content of about 7 wt %, about 7.25 wt %, about 7.5 wt %, about 7.7 wt %, about 8 wt %, about 8.5 wt %, or about 9 wt %. The gelatin capsule may have moisture content in a range of about 6 wt % to about 16 wt %. The actual moisture content of the capsule may be in any increments within the range.

In some embodiments, the gelatin capsule having micronized colistimethate sodium powder may have a minimum critical moisture content of about 6 wt % and a maximum critical moisture content of about 16 wt %. In other embodiments, the gelatin capsule has a minimum critical moisture content of about 6 wt % and a maximum critical moisture content of about 12 wt %, or a minimum critical moisture content of about 8 wt % and a maximum critical moisture content of about 10 wt %.

The micronized colistimethate sodium powder present in the gelatin capsules may have a minimum critical moisture content of about 0.1 wt % and maximum critical moisture content of about 16 wt %, a minimum critical moisture content of about 5 wt % and a maximum critical moisture content of about 16 wt %, or a minimum critical moisture content about 6 wt % and a maximum critical moisture content of about 10 wt %.

In certain embodiments, the minimum RH of the gelatin capsule may be above 2% RH±5% RH, such as, e.g., above 2% RH, above 4% RH, above 6% RH, above 10% RH, above 12% RH, above 15% RH, above 25% RH, above 30% RH, above 40% RH, above 48% RH, ±5% RH at 23° C., ±2° C. In some embodiments, the minimum. RH of the capsule is at 25° C., 26° C., 28° C. or 30° C., ±2° C.

The maximum RH of the gelatin capsule may be less than 75% RH, ±5% RH, such as, for example, less than 50% RH, less than 40% RH, less than 30% RH, less than 20% RH, less than 10% RH, less than 5% RH, ±5% RH at 23° C., ±2° C. In some embodiments, the maximum RH of the capsule is at about 25° C., 26° C., 28° C. and 30° C., ±2° C. The relative humidity may be present in a range of about 2% RH to about 75% RH. The actual relative humidity may be present in any increments within the range.

The gelatin capsule should be pre-equilibrated at about the maximum RH to ensure that the water content of colistimethate sodium powder remains below its maximum critical moisture content. Preferably, the pre-equilibration RH is selected to be below the maximum RH for the capsule such that mechanical performance of the capsule is not compromised. The capsule filling environment is maintained at RH below or at the pre-equilibration RH for the capsule for at least 24 hours.

In other embodiments, the gelatin capsule may be PEG-based. Such PEG-based gelatin capsules having micronized colistimethate sodium powder may have a moisture content of about 5 wt %, about 5.5 wt %, about 5.9 wt %, about 6.5 wt %, about 7 wt %, about 7.5 wt %, about 7.75 wt %, about 8 wt %, or about 9 wt %. The PEG-based gelatin capsule may have moisture content in a range of about 5 wt % to about 15 wt %. The actual moisture content of the capsule may be in any increments within the range.

In certain embodiments, the PEG-based gelatin capsule having micronized colistimethate sodium powder may have a minimum critical moisture content of about 5 wt % and a maximum critical moisture content of about 15 wt %. In other embodiments, the minimum critical moisture content of the capsule is about 6 wt % and the maximum critical moisture content the capsule of about 14 wt %. The minimum critical moisture content of the capsule may be about 7 wt % and the maximum critical moisture content may be about 12 wt %. The maximum critical moisture content of the capsule may also be about 10 wt %.

The minimum RH of the PEG-based gelatin capsule may be above 2% RH, ±5% RH, such as, e.g., above 2% RH, above 4% RH, above 6% RH, above 10% RH, above 12% RH, above 15% RH, above 25% RH, above 35% RH, above 45% RH, ±5% RH at 23° C., ±2° C. In some embodiments, the minimum RH of the capsule is at 25° C., 26° C., 28° C. and 30° C., ±2° C.

The maximum RH of the capsule may be less than 50% RH, ±5% RH, such as, for example, less than 50% RH, less than 40% RH, less than 30% RH, less than 20% RH, less than 10% RH, less than 5% RH, ±5% RH at 23° C., ±2° C. In some embodiments, the maximum RH of the capsule is at about 25° C., 26° C., 28° C. and 30° C., ±2° C. The relative humidity may be present in a range of about 2% RH to about 75% RH. The actual relative humidity may be present in any increments within the range.

In one embodiment of the present invention, a HPMC capsule having micronized colistimethate sodium powder may have a moisture content of about 0.5 wt %, about 1 wt %, about 1.4 wt %, about 2 wt %, about 2.25 wt %, about 2.8 wt %, about 3 wt %, about 3.5 wt %, about 3.75 wt %, about 4 wt %, about 4.5 wt %, about 5 wt %, about 5.5 wt %, about 5.8 wt %, about 7 wt %. The HPMC capsule may have moisture content in a range of about 0.1 wt % to about 10 wt %. The actual moisture content of the capsule may be in any increments within the range.

In other embodiments, the capsule may be an HPMC capsule having micronized colistimethate sodium powder, which may have a minimum critical moisture content of about 0.1 wt % and a maximum critical moisture content of about 10 wt %. Alternatively, the minimum critical moisture content may be about 1 wt % and the maximum critical moisture content about 8 wt %. The minimum critical moisture content of the HPMC capsule having micronized colistimethate sodium powder may be about 1 wt % and the maximum critical moisture content is about 5 wt %, or—the minimum critical moisture content is about 2.5 wt % and the maximum critical moisture content is about 7 wt %.

The minimum critical moisture content of the HPMC capsule may be about 0.5 wt %, about 0.75 wt %, about 1 wt %, about 2 wt % or about 3 wt %.

The maximum critical moisture content of the HPMC capsule may be about 10 wt %, about 9 wt %, about 8 wt %, about 7 wt %, about 6 wt %, or about 5 wt %.

The minimum RH of the HPMC capsule may be above 2% RH, ±5% RH, such as, for example, above 2% RH, above 4% RH, above 6% RH, above 10% RH, above 12% RH, above 15% RH, above 25% RH, above 35% RH, above 45% RH, ±5% RH at 23° C. In some embodiments, the minimum RH of the capsule is at 25° C., 26° C., 28° C. and 30° C., +2° C.

The maximum RH of the HPMC capsule may be less than 50% RH, ±5% RH, such as, e.g., less than 50% RH, less than 40% RH, less than 30% RH, less than 20% RH, less than 10% RH, less than 5% RH, ±5% RH at 23° C. In some embodiments, the maximum RH of the capsule is at about 25° C., 26° C., 28° C. and 30° C., ±2° C. The relative humidity may be present in a range of about 2% RH to about 75% RH. The actual relative humidity may be present in any increments within the range.

By carefully controlling the conditions under which capsules are filled, the final moisture level of colistimethate sodium powder can be kept to below about 15 wt %, preferably from about 0.1 wt % to about 10 wt %. The humidity level is preferably below about 45% RH, more preferably below about 35% RH, most preferably below about 30% RH. The low moisture level is important for product stability, as it enables the product to be filled with minimal static effects.

The amount of composition contained in the capsule will depend upon the desired dosage. Preferably, the capsule has from about 10 milligrams to about 200 milligrams, more preferably about 30 milligrams to about 150 milligrams of the colistin sulphomethate sodium, most preferably about 120 milligrams to about 130 milligrams. The colistimethate sodium may be delivered with or without a carrier. If a carrier is used, then a larger amount of the mix of carrier and pharmaceutical is required. Preferably, capsule should have a larger dose of drug than the amount which will actually be delivered to the lungs.

Dosages are usually expressed in "International Units" or "IU". 80 mg of colistin sulphomethate is equivalent to approximately 1 million IU of colistin sulphomethate. One unit of colistin sulphomethate is contained in 0.00007874 mg of the first International Reference Preparation (1966) of colistin sulphomethate. Children with cystic fibrosis may be treated with nebulised colistimethate sodium at a level of 500,000 units, twice daily. The respirable fraction from a conventional nebuliser (CR 50 System 22) is approximately 9 mg of colistimethate sodium from a 500,000 unit dose. This can be tested using a multistage impinger and measuring mass collected at stages 3 and 4.

A preferred device for delivering the pharmaceutical composition according to the present invention is the Turbospin® originating from PH&T. This device uses a gelatin capsule which is pierced in the bottom by a single metal needle. When the patient inhales through the mouthpiece, air is drawn in through the tangentially ranged slits around the chamber. This spins the capsule and throws out the contents into the airstream. A flip top on the device allows up to three spare capsules to be stored.

Another preferred device for delivering the pharmaceutical composition is the Aerohaler® from Boehringer Ingelheim. This device uses a hard gelatin capsule which is pierced by two metal needles in the side of a capsule. When the patient inhales through the mouthpiece, air enters the bottom of the chamber causing the capsule to spin and throw out its contents into the airstream. The unit holds six capsules in a carousel cartridge. When all six capsules have been used, the unit locks and it must be re-loaded. Other devices known in the art for delivery of encapsulated powders by inhalation can be used.

The capsule keeps the powder at the preferred moisture content and in a flowable form. Capsules should preferably be designed to protect their contents from light, e.g., they should be opaque or the capsules may be translucent and packed and/or stored in opaque containers, e.g., coloured or covered containers, or metal foil.

Proper placement of the capsule in the device, as well as, the manner of piercing used by the device may include, for example, angulated piercing, placing the capsule head first, placing the flat end of the capsule first, piercing on the flat end may decrease the rate of breakage of the capsule. Each example is a separate embodiment of the present invention.

Traditionally the colistimethate sodium must be stored in an airtight container, and with no moisture. However, it has now been found that a critical level of moisture improves flow and does not affect the compound stability. According to the European Pharmacopeia ($7^{th}$ Edition, 2013, pages 1762-1763) there is a maximum limit for moisture content of colistimethate sodium raw non-micronized material of about 5.0 wt %. Tests have shown that micronized powder product according to the present invention stored with a moisture content of from about 0.1 wt % to about 10 wt % over a five year period has no loss in activity and remains stable.

The invention is further described by reference to the following examples, illustrated by the following figures. The following examples are merely illustrative and should not be construed as limiting the scope of the embodiments in any way as many variations and equivalents that are encompassed by these embodiments will become apparent to those skilled in the art upon reading the present disclosure.

EXAMPLES

Example 1

Micronized colistimethate sodium was produced by fluidised energy milling using a Hosokawa Alpine mill of powdered colistimethate sodium having an average particle size of approximately 100 micrometres supplied by Dumex Pharmaceuticals. A sample of the micronized colistimethate sodium was suspended in chloroform and the particle size was analysed by a laser counter. FIG. 1 shows the range of particle sizes of the micronized colistin.

Example 2

Gelatin pharmaceutical capsules (standard size 2) were obtained from Shionogi Qualicaps. The capsules were filled using a standard dosator (Zanassi LZ64) under controlled temperature and humidity conditions (17° C., 10%-15% RH). Colistimethate sodium was filled into the capsules either as pure micronized powder or together with a lactose carrier (lactose monohydrate lactochem pharmaceutical grade from Borculo Whey Products). The fills were as shown in Table 1.

TABLE 1

| Run Number | Mix Used | Total Fill |
|---|---|---|
| 1 | Colistin | 125 mg |
| 2 | Colistin/Lactose (1:1) | 165 mg |

TABLE 1-continued

| Run Number | Mix Used | Total Fill |
|---|---|---|
| 3 | Colistin/Lactose (2:1) | 140 mg |
| 4 | Colistin/Lactose (4:1) | 130 mg |
| 5 | Colistin | 125 mg |

When colistimethate sodium is used alone, it flows well. Filling weights are standard. If a mixture of colistin to lactose as in Run 2 is used then the mixed powder flows well through the machine but there is sticking of the components in the capsule filling machine. Sticking reduces in Runs 3 and 4. Tests found respirable fractions in the region of 16 to 20 milligrams. This is the mass of colistimethate sodium collected on stages 3 and 4 of the multistage liquid impinger and equates to particles having a size less than about 3 to 4 micrometres.

Example 3

Filled capsules produced from Runs 1 to 4 above were stored for nine months under various humidity conditions. There was no degradation or clumping of the colistin sulphomethate sodium. There was no noticeable clumping of colistimethate sodium on the capsule walls.

Example 4

Micronized colistimethate sodium powder was stored under sealed conditions at 25° C. and 60% RH with a moisture content of 8 wt % for five years. The level of free colistin, a toxic degradation product was below about 5 wt %, indicating a very low level of degradation.

Example 5

Aliquots of colistimethate sodium encapsulated in gelatin capsules were stored in relative humidity ranging from about 20% RH to about 80% RH at ambient temperature conditions. Encapsulated colistimethate sodium was tested for moisture content and piercing performance at several time points. For example, the capsules were tested at 23° C. at 30% RH, 23° C. at 40% RH, 23° C. at 48% RH, 23° C. at 75% RH at different time points such as 1, 2, 4, and 24 hrs. Storage conditions were generated using qualified stability chambers set at the target temperature 23° C.±2° C. and the set relative humidity ±5% RH. Ambient laboratory conditions were determined to be at about 23° C.±2° C., 48% RH. Ambient conditions were verified using calibrated NIST thermo-Hygrometers. Average moisture content of colistimethate sodium as well as the moisture content of gelatin capsules was determined using Karl-Fisher determination.

Figure 4:
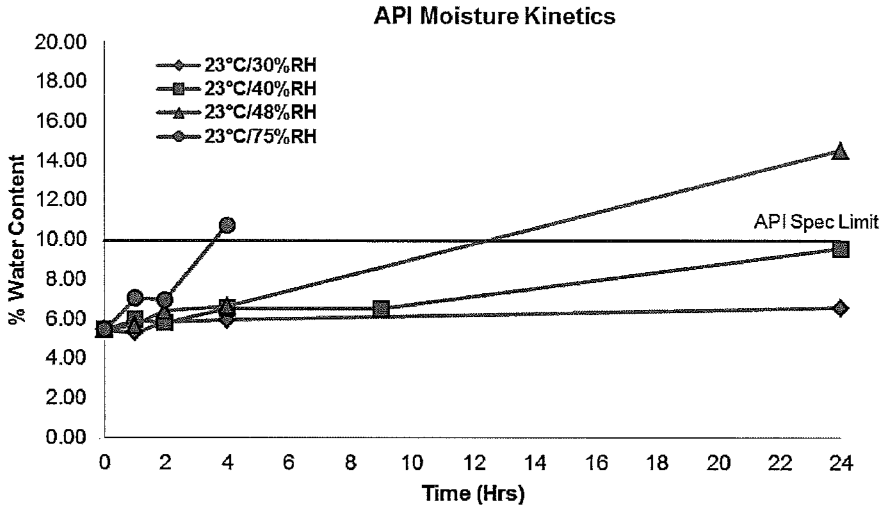
FIG. 4 shows moisture content of colistimethate sodium as a function of time, relative humidity and storage conditions.
Figure 5:
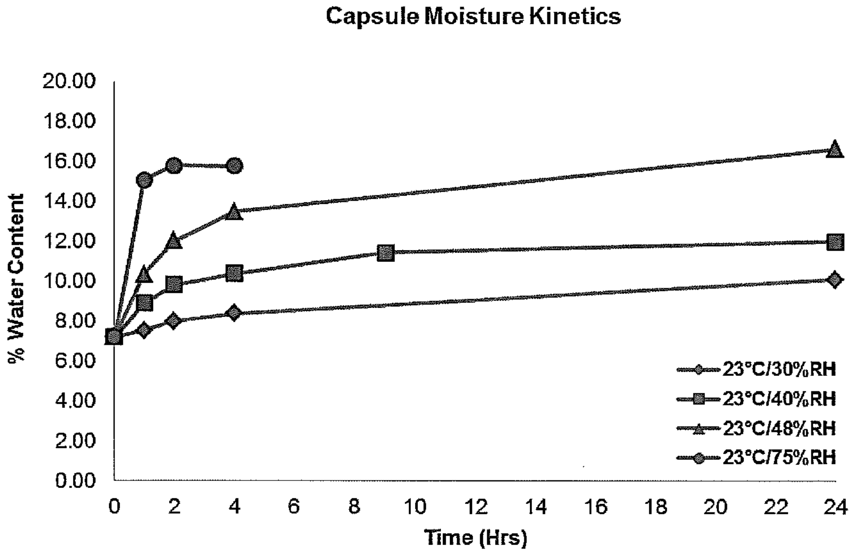
FIG. 5 shows moisture content of gelatin capsule at various storage and relative humidity conditions.

Table 2 below shows the water content (KF) of colistimethate sodium powder and gelatin capsules in various storage conditions. FIG. 4 shows an example of moisture content of colistimethate sodium as a function of time, relative humidity and storage condition. FIG. 5 shows an example of moisture content of gelatin capsule at various storage and relative humidity conditions.

TABLE 2

| | | Water Content (KF) (n = 3) | |
|---|---|---|---|
| Condition | Time (hr) | API | Capsule |
| 23° C./30% RH | 0 | 5.44 | 7.19 |
| | 1 | 5.28 | 7.52 |
| | 2 | 5.85 | 7.98 |
| | 4 | 5.94 | 8.38 |
| | 24 | 6.54 | 10.09 |
| 23° C./40% RH | 0 | 5.44 | 7.19 |
| | 1 | 5.96 | 8.90 |
| | 2 | 5.81 | 9.82 |
| | 4 | 6.51 | 10.37 |
| | 9 | 6.50 | 11.43 |
| | 24 | 9.54 | 12.00 |
| 23° C./48% RH | 0 | 5.44 | 7.19 |
| | 1 | 5.68 | 10.35 |
| | 2 | 6.39 | 12.01 |
| | 4 | 6.64 | 13.49 |
| | 24 | 14.49 | 16.63 |
| 23° C./75% RH | 0 | 5.44 | 7.19 |
| | 1 | 7.04 | 15.08 |
| | 2 | 6.96 | 15.78 |
| | 4 | 10.74 | 15.75 |

Figure 6:
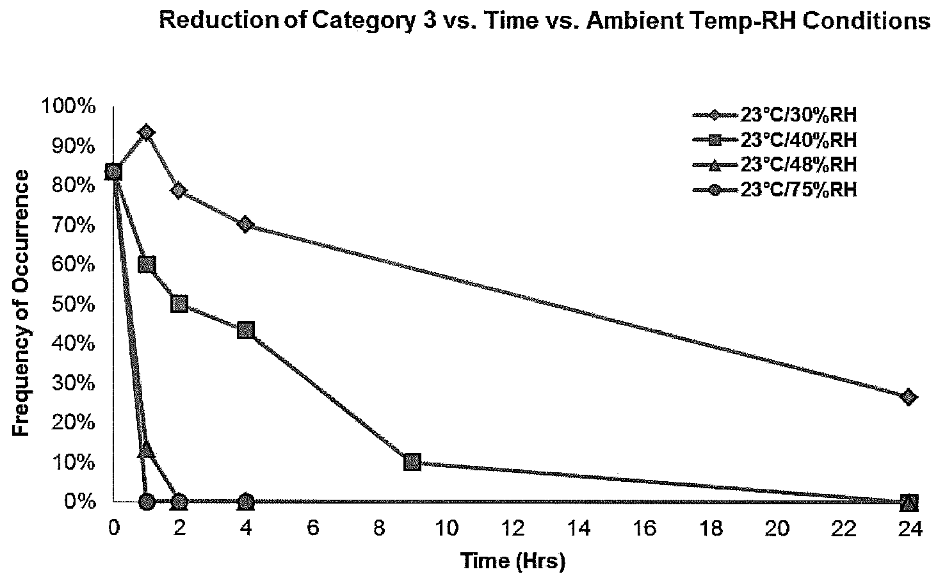
FIG. 6 shows the frequency of category 3 piercing of gelatin capsules as a function of time and storage conditions.

Gelatin capsules were tested to determine capsule shell piercing. Observed capsule shell piercings were categorized in three classes. In category 1, the capsule was pierced to represent two neat holes formed in the body or on the head during actuation while preserving the mechanical integrity of the capsule. In category 2, the capsule was pierced with two clear holes with minor cracking. In category 3, the capsule was pierced to cause a big hole or fragmentation of the capsule. Once a capsule was pierced with a device, for example, Turbospin™ device, the capsule was opened, visually inspected and graded based on the categorized rating scale described herein. Table 3 shows piercing categories for the capsules by time point and conditions. FIG. 6 shows an example of frequency of category 3 piercing of gelatin capsules as a function of time and relative humidity.

TABLE 3

| | | Piercing | | | | | |
|---|---|---|---|---|---|---|---|
| | | Device#1 | | Device#2 | | Device#3 | |
| Condition | Time (HRS) | Head Down | Head Up | Head Down | Head Up | Head Down | Head Up |
| 23° C./30% RH | 0 | 3 | 3 | 1 | 2 | 3 | 3 |
| | | 3 | 3 | 3 | 3 | 3 | 3 |
| | | 3 | 2 | 3 | 2 | 3 | 3 |
| | | 3 | 3 | 3 | 3 | 3 | 3 |
| | | 3 | 3 | 2 | 3 | 3 | 3 |
| | 1 | 3 | 3 | 3 | 3 | 3 | 3 |
| | | 3 | 3 | 3 | 3 | 3 | 3 |
| | | 3 | 2 | 3 | 3 | 3 | 3 |
| | | 3 | 3 | 3 | 3 | 3 | 2 |
| | | 3 | 3 | 3 | 3 | 3 | 3 |
| | 2 | 2 | 3 | 3 | 3 | 3 | 3 |

TABLE 3-continued

| | | Piercing | | | | | |
|---|---|---|---|---|---|---|---|
| | | Device#1 | | Device#2 | | Device#3 | |
| Condition | Time (HRS) | Head Down | Head Up | Head Down | Head Up | Head Down | Head Up |
| | | 3 | 3 | 3 | 3 | 3 | 2 |
| | | 3 | 3 | 3 | 3 | 3 | 2 |
| | | 2 | 3 | 3 | 3 | 3 | 2 |
| | | NT | NT | 3 | 3 | 3 | 2 |
| | 4 | 3 | 2 | 3 | 2 | 3 | 3 |
| | | 3 | 3 | 2 | 3 | 3 | 3 |
| | | 3 | 3 | 2 | 3 | 3 | 2 |
| | | 3 | 3 | 2 | 3 | 3 | 3 |
| | | 3 | 2 | 2 | 3 | 3 | 1 |
| | 24 | 2 | 1 | 2 | 3 | 2 | 3 |
| | | 2 | 1 | 3 | 3 | 2 | 3 |
| | | 2 | 3 | 3 | 1 | 3 | 2 |
| | | 2 | 1 | 2 | 1 | 2 | 2 |
| | | 2 | 1 | 2 | 2 | 2 | 2 |
| 23° C./40% RH | 0 | 3 | 3 | 1 | 2 | 3 | 3 |
| | | 3 | 3 | 3 | 3 | 3 | 3 |
| | | 3 | 2 | 3 | 2 | 3 | 3 |
| | | 3 | 3 | 3 | 3 | 3 | 3 |
| | | 3 | 3 | 2 | 3 | 3 | 3 |
| | 1 | 2 | 3 | 3 | 3 | 3 | 3 |
| | | 2 | 3 | 2 | 2 | 3 | 2 |
| | | 2 | 2 | 2 | 3 | 3 | 2 |
| | | 3 | 3 | 3 | 3 | 2 | 3 |
| | | 3 | 3 | 2 | 3 | 2 | 3 |
| | 2 | 2 | 3 | 3 | 3 | 2 | 3 |
| | | 3 | 3 | 2 | 3 | 2 | 3 |
| | | 2 | 3 | 2 | 3 | 2 | 3 |
| | | 3 | 3 | 2 | 3 | 3 | 2 |
| | | 3 | 2 | 2 | 3 | 2 | 2 |
| | 4 | 2 | 1 | 3 | 3 | 2 | 2 |
| | | 2 | 3 | 2 | 3 | 2 | 1 |
| | | 3 | 2 | 3 | 2 | 3 | 2 |
| | | 2 | 3 | 3 | 2 | 2 | 3 |
| | | 3 | 3 | 2 | 3 | 2 | 2 |
| | 9 | 2 | 1 | 3 | 2 | 2 | 1 |
| | | 2 | 1 | 1 | 2 | 2 | 1 |
| | | 3 | 2 | 1 | 1 | 2 | 3 |
| | | 2 | 1 | 2 | 2 | 2 | 1 |
| | | 1 | 1 | 2 | 1 | 1 | 1 |
| | 24 | 2 | 1 | 1 | 2 | 2 | 1 |
| | | 1 | 1 | 2 | 1 | 1 | 1 |
| | | 2 | 1 | 2 | 1 | 1 | 1 |
| | | 1 | 1 | 1 | 1 | 1 | 1 |
| | | 1 | 1 | 2 | 1 | 1 | 1 |
| 23° C./48% RH | 0 | 3 | 3 | 1 | 2 | 3 | 3 |
| | | 3 | 3 | 3 | 3 | 3 | 3 |
| | | 3 | 2 | 3 | 2 | 3 | 3 |
| | | 3 | 3 | 3 | 3 | 3 | 3 |
| | | 3 | 3 | 2 | 3 | 3 | 3 |
| | 1 | 2 | 2 | 2 | 1 | 2 | 2 |
| | | 3 | 1 | 2 | 1 | 3 | 2 |
| | | 2 | 1 | 2 | 1 | 2 | 1 |
| | | 1 | 2 | 2 | 2 | 2 | 1 |
| | | 2 | 3 | 2 | 2 | 2 | 3 |
| | 2 | 2 | 1 | 1 | 1 | 1 | 1 |
| | | 1 | 1 | 1 | 1 | 1 | 1 |
| | | 2 | 1 | 2 | 1 | 1 | 1 |
| | | 1 | 2 | 1 | 1 | 2 | 1 |
| | | 1 | 1 | 1 | 1 | 2 | 2 |
| | 4 | 1 | 1 | 1 | 1 | 2 | 1 |
| | | 2 | 1 | 1 | 1 | 1 | 1 |
| | | 1 | 1 | 2 | 1 | 1 | 1 |
| | | 1 | 1 | 1 | 1 | 1 | 1 |
| | | 2 | 1 | 1 | 1 | 1 | 1 |
| | 24 | 1 | 1 | 1 | 1 | 1 | 1 |
| | | 1 | 1 | 1 | 1 | 1 | 1 |
| | | 1 | 1 | 1 | 1 | 1 | 1 |
| | | 1 | 1 | 1 | 1 | 1 | 1 |
| | | 1 | 1 | 1 | 1 | 1 | 1 |
| 23° C./75% RH | 0 | 3 | 3 | 1 | 2 | 3 | 3 |
| | | 3 | 3 | 3 | 3 | 3 | 3 |
| | | 3 | 2 | 3 | 2 | 3 | 3 |
| | | 3 | 3 | 3 | 3 | 3 | 3 |
| | | 3 | 3 | 2 | 3 | 3 | 3 |

TABLE 3-continued

| Condition | Time (HRS) | Piercing Device#1 Head Down | Device#1 Head Up | Device#2 Head Down | Device#2 Head Up | Device#3 Head Down | Device#3 Head Up |
|---|---|---|---|---|---|---|---|
| | 1 | 2 | 1 | 1 | 1 | 2 | 1 |
| | | 2 | 1 | 1 | 1 | 1 | 1 |
| | | 1 | 1 | 1 | 1 | 1 | 1 |
| | | 1 | 1 | 1 | 1 | 1 | 1 |
| | | 2 | 2 | 1 | 1 | 1 | 1 |
| | 2 | 1 | 1 | 1 | 1 | 1 | 1 |
| | | 1 | 1 | 1 | 1 | 1 | 1 |
| | | 1 | 1 | 1 | 1 | 1 | 1 |
| | | 1 | 1 | 1 | 1 | 1 | 1 |
| | | 1 | 1 | 1 | 1 | 1 | 1 |
| | 4 | 1 | 1 | 1 | 1 | 1 | 1 |
| | | 1 | 1 | 1 | 1 | 1 | 1 |
| | | 1 | 1 | 1 | 1 | 1 | 1 |
| | | 1 | 1 | 1 | 1 | 1 | 1 |
| | | 1 | 1 | 1 | 1 | 1 | 1 |

Table 4 below shows the equilibrium time per storage condition, based on degree of reduction of category 3 piercing and colistimethate water content.

TABLE 4

| Condition | Equilibration Time |
|---|---|
| 23° C./30% RH | At least 24 Hours |
| 23° C./40% RH | NLT 9 Hours<br>NMT 24 Hours |
| 23° C./48% RH | NLT 2 Hours<br>NMT 12 Hours |
| 23° C./75% RH | NLT 1 Hour<br>NMT 3 Hours |

Example 6

Figure 7:
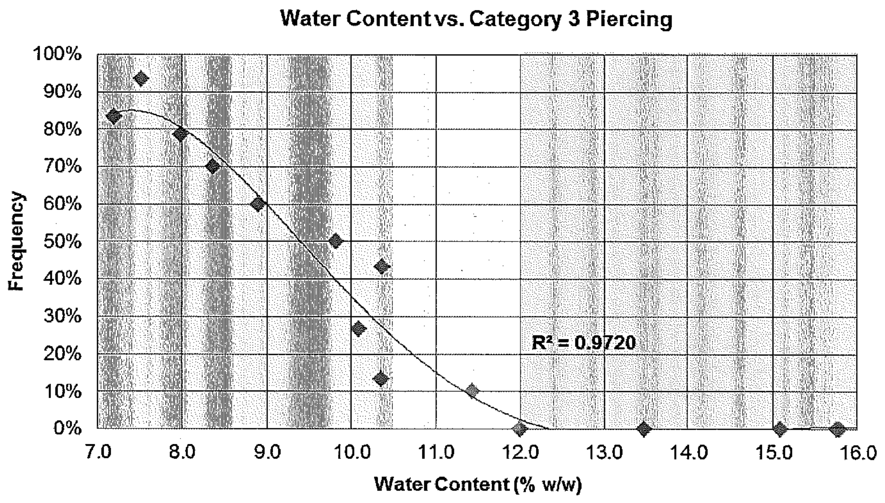
FIG. 7 shows reductions in category 3 piercings of gelatin capsules.

As illustrated in Example 5 and as shown in FIGS. 4-6, moisture content of the capsule shell may have a direct impact on the capsule shell piercing of the gelatin capsule having colistimethate sodium powder. FIG. 7 shows an example of a range where the greatest reduction of category 3 piercings was observed in gelatin capsules. FIG. 7 also shows moisture content of the capsules against frequency of category 3 piercings. The gelatin capsule water content is approximately 12 wt %, above which the capsule shell is pliable enough to withstand the force of the actuating pins and a category 3 piercing is unlikely to be observed. As shown in FIG. 7, the frequency of category 3 piercing increases below the moisture content of about 10.5 wt %.

Example 7

Capsule breakage rate of three different types of capsules were determined. Table 5 shows water content of capsule shell and the average breakage rate for the capsules.

TABLE 5

| Capsule type | Relative Humidity | Water content of the capsule shell | Category 3 piercing |
|---|---|---|---|
| Gelatin Capsules | 11 | 6.5 | 11/12 |
| | 17 | 8.9 | 8/12 |
| | 23 | 10.6 | 5/12 |
| | 33 | 12.7 | 0/12 |
| | 43 | 14.6 | 0/12 |
| HPMC capsules | 11 | 1.4 | 0/12 |
| | 17 | 2.1 | 0/12 |
| | 23 | 2.8 | 0/12 |
| | 33 | 4.0 | 0/12 |
| | 43 | 5.3 | 0/12 |
| PEG Based Gelatin capsules | 11 | 5.9 | 0/12 |
| | 17 | 8.2 | 0/12 |
| | 23 | 10.1 | 0/12 |
| | 33 | 12.5 | 0/12 |
| | 43 | 14.3 | 0/12 |

Capsules were exposed to different relative humidity and storage conditions. For example, capsules were exposed to conditions ranging from 11% RH to 43% RH at 25° C. Capsule shell moisture content of each type of capsule was determined.

Under identical conditions, capsule shell water content was the highest in gelatin capsules followed by PEG based gelatin capsules and HPMC capsules. For about the same water content, breakage rate was higher for the gelatin capsules compared to PEG based gelatin capsules. HPMC capsules exhibited low breakage, as shown in Table 5, at very low water content.

Example 8

In one clinical trial, the absorption of the powdered colistimethate sodium into the airways of the lungs was measured (specific airway conductance). It was found that 80% of patients, inhaling the micronized dry powder colistin sulphomethate sodium, were able to mobilise 80 milligrams of the drug, i.e., 1 mega unit. This is a very high uptake, and more than would be expected from a powdered drug. The powder does not cause irritation, and thus construction, of the lungs. In a second trial, patients were given a premedication dose of 200 micrograms of salbutamol. This appeared to improve airway conductance. In an alternative medication regime, the salbutamol can be mixed into the same capsule as the colistin sulphomethate sodium. A further trial compared specific airway conductance, as measured by whole body plethysmography, of traditional nebulised colistimethate sodium and dry powder and the trial did not show any noticeable difference.

EQUIVALENTS

While the embodiments have been depicted and described by reference to exemplary embodiments, such a reference does not imply a limitation on the scope, and no such limitation is to be inferred. The embodiments are capable of considerable modification, alteration, and equivalents in form and function, as will occur to those ordinarily skilled in the pertinent arts having the benefit of this disclosure.

The depicted and described embodiments are exemplary only, and are not exhaustive of the scope.

All references cited herein are hereby incorporated by reference in their entirety.

We claim:

1. A powder composition consisting of: micronized powder particles of colistimethate sodium wherein at least 50% by volume of the micronized particles have a diameter of less than 7micrometers but not less than 3 micrometers, and wherein the powder composition has a total moisture content of from 5 to 10% by weight, for use in the treatment of a pulmonary infection by powder inhalation, wherein the colistimethate sodium is not separated into component form.

2. The powder composition according to claim 1 wherein 10% by volume of the micronized powder particles of colistmethate sodium have a particle size of less than 3 micrometers but not less than 1.5 micrometers.

3. The powder composition according to claim 1, wherein the micronized powder particles of colistimethate sodium are present with a minimum critical moisture content of about 6 wt % and a maximum critical moisture content of about 10 wt %.

4. The powder composition according to claim 1, wherein the micronized powder particles of colistimethate sodium are present with a minimum critical moisture content of about 5.5 wt % and a maximum critical moisture content of about 8 wt %.

* * * * *